United States Patent
Komatsuki et al.

(10) Patent No.: US 9,975,831 B2
(45) Date of Patent: May 22, 2018

(54) METHOD FOR PRODUCING ETHER COMPOUND

(71) Applicant: TAKASAGO INTERNATIONAL CORPORATION, Tokyo (JP)

(72) Inventors: Yasuhiro Komatsuki, Hiratsuka (JP); Kenya Ishida, Tokyo (JP); Kenji Yagi, Hiratsuka (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days. days.

(21) Appl. No.: 14/376,988

(22) PCT Filed: Feb. 5, 2013

(86) PCT No.: PCT/JP2013/052601
§ 371 (c)(1),
(2) Date: Aug. 6, 2014

(87) PCT Pub. No.: WO2013/118717
PCT Pub. Date: Aug. 15, 2013

(65) Prior Publication Data
US 2015/0011799 A1   Jan. 8, 2015

(30) Foreign Application Priority Data
Feb. 9, 2012   (JP) .................. 2012-026444

(51) Int. Cl.
*C07C 41/01* (2006.01)
(52) U.S. Cl.
CPC .......... *C07C 41/01* (2013.01); *C07C 2601/12* (2017.05); *C07C 2602/42* (2017.05)
(58) Field of Classification Search
None
See application file for complete search history.

(56) References Cited

U.S. PATENT DOCUMENTS

| 4,484,009 A | 11/1984 | Ghenassia et al. |
| 5,399,631 A | 3/1995 | Egawa et al. |

FOREIGN PATENT DOCUMENTS

| EP | 1022266 A1 | 7/2000 |
| JP | 58-189129 A | 11/1983 |
| JP | 6-128184 A | 5/1994 |
| JP | 9-40593 A | 2/1997 |

OTHER PUBLICATIONS

MacKenzie et al., J. Org. Chem. Jul. 20, 1955, 1695-1701.*

M. Verzele, et al., "1072. A General Synthesis of Ethers. Hydrogenation of ketones in presence of platinum oxide in alcoholic acid leads to ethers with good yields.", Journal of Chemical Society, pp. 5598-5600, (1963).
Shigeo Nishimura, et al., "Reactions of Cycloalkanones in the Presence of Platinum-metal Catalysts and Hydrogen", Chemical Communication, pp. 422-423, (1967).
Michael P. Doyle, et al., "Silane Reductions in Acidic Media. I. Reduction of Aldehydes and Ketones in Alcoholic Acidic Media. A General Synthesis of Ethers", Journal of the American Chemical Society, pp. 3659-3661, (1972).
Olah, G.A. et al., "Nafion-H catalyzed reductive cleavage of acetals and ketals to ethers with triethylsilane", Journal of Organic Chemistry, 1986, vol. 51, No. 14, pp. 2826-2828.
Howard, W. L., et al, "Hydrogenolysis of Ketals", Journal of Organic Chemistry, vol. 26, 1961, pp. 1026-1028.
Fujii,Y. et al., "A convenient catalytic method for the synthesis of ethers from alcohols and carbonyl compounds", Bulletin of the Chemical Society of Japan, 2005, vol. 78, No. 3, pp. 456-463, Publish on the web Mar. 11, 2005.
Anzalone,P.W. et al., "Bismuth compounds in organic synthesis. A one-pot synthesis of homoallyl ethers and homoallyl acetates from aldehydes catalyzed by bismuth triflate", Journal of Organic Chemistry, 2005, vol. 70, No. 6, pp. 2091-2096, Published on the web Feb. 10, 2005.
International Search Report for PCT/JP2013/052601 dated May 7, 2013 [PCT/ISA/210].
Written Opinion for PCT/JP2013/052601 dated May 7, 2013 [PCT/ISA/237].
Search Report dated Aug. 5, 2015, issued by the European Patent Office in counterpart European Patent Application No. 13747278.3.
Communication dated Dec. 1, 2015, from the Japanese Patent Office in counterpart application No. 2012-026444.

* cited by examiner

*Primary Examiner* — Sudhakar Katakam
*Assistant Examiner* — Ana Z Muresan
(74) *Attorney, Agent, or Firm* — Sughrue Mion, PLLC

(57) ABSTRACT

An object of the present invention is to provide a method for producing an ether compound easily in a small number of steps at lower costs in high yields.
The present invention relates to a method in which the ether compound represented by the general formula (1) is produced by reacting the specific carbonyl compound specified in the general formula (2) and the specific dialkoxy compound specified in the general formula (3) with hydrogen in the presence of a hydrogenation catalyst and an acidic substance to perform hydrogenation.

[Chem. 1]

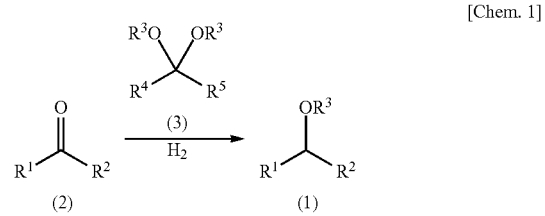

3 Claims, No Drawings

METHOD FOR PRODUCING ETHER COMPOUND

CROSS REFERENCE TO RELATED APPLICATIONS

This application is a National Stage of International Application No. PCT/JP2013/052601 filed Feb. 5, 2013, claiming priority based on Japanese Patent Application No. 2012-026444 filed Feb. 9, 2012, the contents of all of which are incorporated herein by reference in their entirety.

TECHNICAL FIELD

The present invention relates to a method for producing an ether compound. More specifically, it relates to a novel production method capable of producing an ether compound useful as a pharmaceutical, an agricultural chemical, a functional material, a fragrance or cosmetic, various chemicals, or its raw material or its synthetic intermediate in high yields with high efficiency.

BACKGROUND ART

Ether compounds have been heretofore widely used as a variety of pharmaceuticals, agricultural chemicals, functional materials, fragrances or cosmetics, components of various chemicals, or their raw materials, their synthetic intermediates and the like. As a method for producing the ether compounds, it has been known that a method of obtaining an ether compound by alkylation of an alcohol compound is useful, and various reagents and reaction modes have been proposed with regard to the alkylation reaction.

On the other hand, as methods for obtaining the ether compounds from carbonyl compounds in one step, for example, there have been known a method of hydrogenating a carbonyl compound and an alcohol compound in the presence of an acidic substance and a hydrogenation catalyst (Non-Patent Documents 1 and 2), a method of treating a carbonyl compound and an alcohol compound with a trialkylsilane under an acidic condition (Non-Patent Document 3), and the other methods.

PRIOR ART DOCUMENTS

Non-Patent Documents

Non-Patent Document 1: Journal of Chemical Society, pp. 5598-5600 (1963)
Non-Patent Document 2: Chemical Communication, pp. 422-423 (1967)
Non-Patent Document 3: Journal of the American Chemical Society, pp. 3659-3661 (1972)

SUMMARY OF THE INVENTION

Problems that the Invention is to Solve

However, in the case of the method of the hydrogenation together with an alcohol compound in the presence of an acidic substance and a hydrogenation catalyst, there is a limitation on a reaction substrate and the yield is not sufficient. Also, in the case of the method of the treatment with a trialkylsilane together with an alcohol compound under an acidic condition, the synthetic reaction using the trialkylsilane is complicated in operation and furthermore, there is a limitation on the reaction substrate and the yield is not sufficient. Therefore, there is room for improvement in the production methods for obtaining the ether compounds in a small number of steps.

Namely, an object of the present invention is to provide a method for producing an ether compound easily in a small number of steps at lower costs in high yields.

Means for Solving the Problems

As a result of extensive studies, the present inventors have found that an ether compound can be produced efficiently in high yields by reacting a carbonyl compound and dialkoxy compound, each having a specific structure, with hydrogen in the presence of a hydrogenation catalyst and an acidic substance to perform hydrogenation, and thus they have accomplished the present invention.

That is, the present invention relates to the following [1] to [4].

[1] A method for producing an ether compound represented by the following general formula (1), comprising a step of reacting a carbonyl compound represented by the following general formula (2) and a dialkoxy compound represented by the following general formula (3) with hydrogen in the presence of a hydrogenation catalyst and an acidic substance to perform hydrogenation:

[Chem. 1]

(2)

wherein $R^1$ is an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent;

$R^2$ is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent; and $R^1$ and $R^2$ may be combined to form a ring,

[Chem. 2]

(3)

wherein $R^3$ is an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent (provided that a group which is eliminated by hydrogenation is excluded);

$R^4$ is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent;

$R^5$ is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, an aralkyl group which may have a substituent, or a group represented by —$OR^3$;

provided that a case where both of $R^4$ and $R^5$ are a hydrogen atom is excluded; and further $R^4$ and $R^5$ may be combined to form a ring,

[Chem. 3]

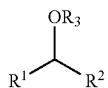

(1)

wherein definitions of $R^1$ to $R^3$ have the same meanings as described above.

[2] The production method according to [1], wherein an alcohol represented by the following general formula (4) is used in combination as an additional component:

$R^3OH$           (4)

wherein a definition of $R^3$ has the same meaning as described above.

[3] The production method according to [1] or [2], wherein the acidic substance is at least one selected from the group consisting of benzenesulfonic acid, p-toluenesulfonic acid, methanesulfonic acid, camphorsulfonic acid, sulfuric acid, trifluoroacetic acid, ferric chloride, zinc chloride, stannic chloride, and zinc bromide.

[4] The production method according to any one of [1] to [3], wherein the hydrogenation catalyst is a heterogeneous hydrogenation catalyst containing at least one metal selected from the group consisting of palladium, iridium, rhodium, ruthenium, nickel, osmium, and platinum.

Advantages of the Invention

The method for producing an ether compound of the present invention is a method for producing an ether compound useful as a pharmaceutical, an agricultural chemical, a functional material, a fragrance or cosmetic, various chemicals, or its raw material or its synthetic intermediate, easily in a small number of steps at lower costs in high yields. Thus, the method is industrially advantageous.

MODE FOR CARRYING OUT THE INVENTION

The present invention will be explained in detail below.

The method for producing an ether compound of the present invention is conducted by the reaction shown below.

As shown in the following chemical formula, an ether compound (1) is obtained by reacting a carbonyl compound represented by the general formula (2) and a dialkoxy compound represented by the general formula (3) with hydrogen in the presence of a hydrogenation catalyst and an acidic substance to perform hydrogenation.

[Chem. 4]

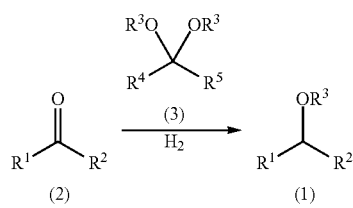

In the formulae (1) to (3), $R^1$ is an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent.

$R^2$ is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent.

Further, $R^1$ and $R^2$ may be combined to form a ring.

$R^3$ is an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent (provided that a group which is eliminated by hydrogenation is excluded).

$R^4$ is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent.

$R^5$ is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, an aralkyl group which may have a substituent, or a group represented by —$OR^3$.

In this regard, however, a case where both of $R^4$ and $R^5$ are a hydrogen atom is excluded. Further, $R^4$ and $R^5$ may be combined to form a ring, The carbonyl compound represented by the following general formula (2), which is a raw material for producing the ether compound in the present invention, will be explained.

[Chem. 5]

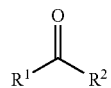

(2)

In the formula (2), $R^1$ is an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent.

$R^2$ is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent. Further, $R^1$ and $R^2$ may be combined to form a ring.

As the alkyl group having 1 to 20 carbon atoms represented by $R^1$ in the general formula (2), an alkyl group having 1 to 10 carbon atoms is preferred. Specific examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and the like.

As the 3- to 8-membered alicyclic group represented by $R^1$ in the general formula (2), a 5- to 7-membered alicyclic group is preferred. Specific examples thereof include a cyclopropyl group, a cyclobutyl group, a cyclopentyl group, a cyclohexyl group, a cycloheptyl group, a cyclooctyl group, and the like.

As the aryl group represented by $R^1$ in the general formula (2), an aromatic monocyclic group, an aromatic polycyclic group, or an aromatic condensed cyclic group, each having 6 to 20 carbon atoms, is preferred. Specific examples thereof include a phenyl group, a naphthyl group, an anthryl group, a phenanthryl group, an indenyl group, and the like. Furthermore, a metallocenyl group such as ferrocenyl group may be exemplified.

As the heterocyclic group represented by $R^1$ in the general formula (2), an aliphatic heterocyclic group and an aromatic heterocyclic group may be mentioned.

As the aliphatic heterocyclic group, examples thereof include 3- to 8-membered, preferably 5- or 6-membered monocyclic, polycyclic, or condensed cyclic ones having 2 to 14 carbon atoms and containing at least one heteroatom, preferably 1 to 3 heteroatoms. As the heteroatom, heteroatoms such as a nitrogen atom, an oxygen atom, and a sulfur atom may be mentioned.

Specific examples of the aliphatic heterocyclic group include an oxiranyl group, an aziridinyl group, a 2-oxopyrrolidyl group, a piperidyl group, a piperadinyl group, a morpholino group, a tetrahydrofuryl group, a tetrahydropyranyl group, a tetrahydrothienyl group, and the like.

On the other hand, as the aromatic heterocyclic group, examples thereof include 5- to 8-membered, preferably 5- or 6-membered monocyclic, polycyclic, or condensed cyclic aromatic heterocyclic (heteroaryl) groups having 2 to 15 carbon atoms and containing at least one heteroatom, preferably 1 to 3 heteroatoms. As the heteroatom, a nitrogen atom, an oxygen atom, a sulfur atom and the like may be mentioned.

Specific examples of the aromatic heterocyclic group include a tetrazinyl group, a furyl group, a thienyl group, a pyridyl group, a pyrinidyl group, a pyrazinyl group, a pyradazinyl group, an imidazoyl group, an oxazoyl group, a thiazoyl group, a benzofuryl group, a benzothienyl group, a quinolyl group, an isoquinolyl group, a quinoxalinyl group, a phthalazinyl group, a quinazolinyl group, a naphthylidinyl group, a cinnolinyl group, a benzimidazoline group, a benzoxazolyl group, a benzothiazolyl group, and the like.

As the aralkyl group represented by $R^1$ in the general formula (2), an aralkyl group having 7 to 20 carbon atoms is preferred. Specific examples thereof include a benzyl group, a 1-phenylethyl group, a 2-phenylethyl group, and the like.

As the alkyl group having 1 to 20 carbon atoms represented by $R^2$ in the general formula (2), an alkyl group having 1 to 10 carbon atoms is preferred. Specific examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and the like.

As the 3- to 8-membered alicyclic group represented by $R^2$ in the general formula (2), a 5- to 7-membered alicyclic group is preferred. Specific examples thereof include a cyclopropyl group, a cyclobutyl group, a cyclopentyl group, a cyclohexyl group, a cycloheptyl group, a cyclooctyl group, and the like.

As the aryl group represented by $R^2$ in the general formula (2), an aromatic monocyclic group, an aromatic polycyclic group, or an aromatic condensed cyclic group, each having 6 to 20 carbon atoms, is preferred. Specific examples thereof include an aromatic monocyclic or polycyclic group such as phenyl group, a naphthyl group, an anthryl group, a phenanthryl group, an indenyl group, and the like. Furthermore, a metallocenyl group such as ferrocenyl group may be exemplified.

As the heterocyclic group represented by $R^2$ in the general formula (2), an aliphatic heterocyclic group and an aromatic heterocyclic group may be mentioned.

As the aliphatic heterocyclic group, examples thereof include 3- to 8-membered, preferably 5- or 6-membered monocyclic, polycyclic, or condensed cyclic ones having 2 to 14 carbon atoms and containing at least one heteroatom, preferably 1 to 3 heteroatoms. As the heteroatom, heteroatoms such as a nitrogen atom, an oxygen atom, and a sulfur atom may be mentioned.

Specific examples of the aliphatic heterocyclic group include an oxiranyl group, an aziridinyl group, a 2-oxopyrrolidyl group, a piperidyl group, a piperadinyl group, a morpholino group, a tetrahydrofuryl group, a tetrahydropyranyl group, a tetrahydrothienyl group, and the like.

On the other hand, as the aromatic heterocyclic group, examples thereof include 5- to 8-membered, preferably 5- or 6-membered monocyclic, polycyclic, or condensed cyclic aromatic heterocyclic (heteroaryl) groups having 2 to 15 carbon atoms and containing at least one heteroatom, preferably 1 to 3 heteroatoms. As the heteroatom, heteroatoms such as a nitrogen atom, an oxygen atom, and a sulfur atom may be mentioned.

Specific examples of the aromatic heterocyclic group include a tetrazinyl group, a furyl group, a thienyl group, a pyridyl group, a pyrinidyl group, a pyrazinyl group, a pyradazinyl group, an imidazoyl group, an oxazoyl group, a thiazoyl group, a benzofuryl group, a benzothienyl group, a quinolyl group, an isoquinolyl group, a quinoxalinyl group, a phthalazinyl group, a quinazolinyl group, a naphthylidinyl group, a cinnolinyl group, a benzimidazoline group, a benzoxazolyl group, a benzothiazolyl group, and the like.

As the aralkyl group represented by $R^2$ in the general formula (2), an aralkyl group having 7 to 20 carbon atoms is preferred. Specific examples thereof include a benzyl group, a 1-phenylethyl group, a 2-phenylethyl group, and the like.

In the case where $R^1$ and $R^2$ are combined to form a ring, the number of carbon atoms in the ring is preferably from 3 to 16. Specific examples thereof include cyclic ketones such as cyclopropanone, cyclobutanone, cyclopentanone, cyclohexanone, cycloheptanone, cyclooctanone, cyclononanone, cyclodecanone, cycloundecanone, cyclododecanone, cyclotridecanone, cyclopentadecanone, and cyclohexadecanone.

Here, the alkyl group having 1 to 20 carbon atoms, the 3- to 8-membered alicyclic group, the aryl group, the heterocyclic group, and the aralkyl group represented by $R^1$ and $R^2$ in the general formula (2) may have a substituent. As the substituent, examples thereof include an alkyl group, an aryl group, an aralkyl group, an alicyclic group, a halogen atom, a hydroxyl group, an alkoxy group, a trisubstituted organosilyl group, an oxycarbonyl group, an acyl group, an acyloxy group, a substituted amino group, a heterocyclic group, a nitro group, and the like.

Here, as the alkyl group as the substituent, examples thereof include alkyl groups having 1 to 6 carbon atoms, such as a methyl group, an ethyl group, an n-propyl group, an isopropyl group, a sec-butyl group, a tert-butyl group, a pentyl group, and a hexyl group.

As the aryl group as the substituent, examples thereof include aryl groups having 6 to 14 carbon atoms, such as a phenyl group, an α-naphthyl group, a β-naphthyl group, an anthryl group, a phenanthryl group, and a biphenyl group.

As the aralkyl group as the substituent, examples thereof include aralkyl groups having 7 to 12 carbon atoms, such as a benzyl group, a 1-phenylethyl group, a 2-phenylethyl group, an α-naphthylmethyl group, and a β-naphthylmethyl group.

As the alicyclic group as the substituent, examples thereof include alicyclic groups having 5 to 8 carbon atoms, such as a cyclopentyl group, a cyclohexyl group, a methylcyclohexyl group, a cycloheptyl group, and a cyclooctyl group.

As the halogen atom as the substituent, examples thereof include a fluorine atom, a chlorine atom, a bromine atom, an iodine atom, and the like.

As the alkoxy group as the substituent, examples thereof include alkoxy groups having 1 to 4 carbon atoms, such as a methoxy group, an ethoxy group, an n-propoxy group, an isopropoxy group, an n-butoxy group, an isobutoxy group, a sec-butoxy group, and a tert-butoxy group.

As the trisubstituted organosiylyl group as the substituent, preferable examples thereof include a trialkylsilyl group such as a trimethylsilyl group, a triethylsilyl group, a triisopropylsilyl group, a dimethylisopropylsilyl group, a diethylisopropylsilyl group, a dimethyl(2,3-dimethyl-2-butyl)silyl group, a tert-butyldimethylsilyl group, or a dimethylhexylsilyl group, and the number of carbon atoms in the alkyl group is preferably from 1 to 6.

As the oxycarbonyl group as the substituent, examples thereof include alkoxycarbonyl groups having 2 to 6 carbon atoms, such as a methoxycarbonyl group and ethoxycarbonyl group, and aryloxycarbonyl groups having 6 to 11 carbon atoms, such as a phenoxycarbonyl group.

As the acyl group as the substituent, examples thereof include acyl groups having 1 to 8 carbon atoms, such as a formyl group, an acetyl group, a propionyl group, an n-butyroyl group, an isobutyroyl group, and a benzoyl group.

As the acyloxy group as the substituent, examples thereof include acyloxy groups having 1 to 8 carbon atoms, such as a formyloxy group, an acyloxy group, a propionyloxy group, an n-butyryloxy group, an isobutyroyloxy group, and a benzoyloxy group.

As the substituted amino group as the substituent, examples thereof include dialkylamino groups in which alkyl groups each having 1 to 12 carbon atoms are separated, such as a dimethylamino group, a diethylamino group, a diisopropylamino group, and a piperidyl group.

As the heterocyclic group as the substituent, examples thereof include aliphatic heterocyclic groups and aromatic heterocyclic groups. Examples of the aliphatic heterocyclic groups include 3- to 8-membered, preferably 5- or 6-membered monocyclic, polycyclic, or condensed cyclic aliphatic heterocyclic groups having 2 to 14 carbon atoms and containing at least one heteroatom, preferably 1 to 3 heteroatoms. As the heteroatom, heteroatoms such as a nitrogen atom, an oxygen atom, and a sulfur atom may be mentioned.

Specific examples of the aliphatic heterocyclic group include an oxiranyl group, an aziridinyl group, a 2-oxopyrrolidyl group, a piperidyl group, a piperadinyl group, a morpholino group, a tetrahydrofuryl group, a tetrahydropyranyl group, a tetrahydrothienyl group, and the like.

On the other hand, as the aromatic heterocyclic group, examples thereof include 5- to 8-membered, preferably 5- or 6-membered monocyclic, polycyclic, or condensed cyclic aromatic heterocyclic (heteroaryl) groups having 2 to 15 carbon atoms and containing at least one heteroatom, preferably 1 to 3 heteroatoms. As the heteroatom, heteroatoms such as a nitrogen atom, an oxygen atom, and a sulfur atom may be mentioned.

Specific examples of the aromatic heterocyclic group include a tetrazinyl group, a furyl group, a thienyl group, a pyridyl group, a pyrinidyl group, a pyrazinyl group, a pyradazinyl group, an imidazoyl group, an oxazoyl group, a thiazoyl group, a benzofuryl group, a benzothienyl group, a quinolyl group, an isoquinolyl group, a quinoxalinyl group, a phthalazinyl group, a quinazolinyl group, a naphthylidinyl group, a cinnolinyl group, a benzimidazoline group, a benzoxazolyl group, a benzothiazolyl group, and the like.

As the carbonyl compound represented by the general formula (2) (hereinafter sometimes referred to as "carbonyl compound (2)") in the present invention, the following compounds may be specifically exemplified.

Aliphatic aldehydes such as acetaldehyde, propionaldehyde, butylaldehyde, n-valeraldehyde, isovaleraldehyde, 2-methylbutanal, n-hexanal, n-heptanal, n-octanal, n-nonanal, 2-methyloctanal, 3,5,5-trimethylhexanal, decanal, undecanal, 2-methyldecanal, dodecanal, 2-methylundecanal, tridecanal, and tetradecanal;

terpene-based aldehydes such as dimethyloctanal, hydroxycitronellal, methoxycitronellal, and POLLENAL II (Kao Corporation, trade name);

alicyclic aldehydes such as octahydro-4,7-mehtanoindenecarboxyaldehyde and SCENTENAL (Firmenich Company, trade name);

aromatic and other aldehydes such as benzaldehyde, p-tolylaldehyde, cuminaldehyde, phenylacetaldehyde, p-methylphenylacetaldehyde, p-isopropylphenylacetaldehyde, hydratropaldehyde, p-methylhydratropaldehyde, p-isopropylhydropropaldehyde, phenylpropionaldehyde, β-methylhydrocinnamic aldehyde, 2-methyl-3-(4-methylphenyl)-propanol, p-tert-butylhydrocinnamic aldehyde, cyclamen aldehyde, p-ethyldimethylhydrocinnamic aldehyde, p-isobutyl-α-methylhydrocinnamic aldehyde, p-tert-butyl-α-methylhydrocinnamic aldehyde, 3-methyl-5-phenylvaleraldehyde, salicylaldehyde, anisaldehyde, o-methoxybenzaldehyde, 2-methyl-3-(p-menthoxyphenyl)-propanal, vanillin, ethylvanillin, methylvanillin, heliotropin, 3-(3,4-methylenedioxyphenyl)-2-methylpropanal, phenoxyacetaldehyde, p-methylphenoxyacetaldehyde, furfural, 5-methylfurfural, and 5-hydroxymethylfurfural;

linear ketones such as 2-pentanone, 3-hexanone, 2-heptanone, 3-heptanone, 4-heptanone, 2-octanone, 3-octanone, 2-nonanone, 3-nonanone, 2-undecanone, methyl isopropyl ketone, ethyl isoamyl ketone, 3-tridecanone, acetoin, butyroin, 3-hydroxymethyl-2-nonanone, diacetyl, 2,3-pentanedione, 2,3-hexanedione, 3,4-hexanedione, 2,3-heptanedione, and acetylisovaleryl;

cyclic ketones such as amylcyclopentanone, 2-cyclopentylcyclopentanone, hexylcyclopentanone, heptylcyclopentanone, trimethylpentanecyclopentanone, cyclotene, 3,5-dimethyl-1,2-cyclopentanedione, 3,4-dimethyl-1,2-cyclopentanedione, o-tert-butylcyclohexanone, p-tert-butylcyclohexanone, 3,3-diemtylcyclohexyl methyl ketone, 2-sec-butylcyclohexanone, p-tert-pentylcyclohexanone, 4-cyclohexyl-4-methyl-2-pentanone, tetrahydroionone, tetrahydromethylionone, 2,4-di-tert-butylcyclohexanone, 2-acetyl-3,3-dimethylnorbornane, PLICATONE (Firmenich Company, trade name), CASHMERAN (IFF Company, trade name), ATRINON (Kao Corporation, trade name), acetyldimethyltetrahydrobenzindane, and CALONE (Pfizer Company, trade name);

terpene-based ketones such as pulegone, diosphenol, menthone, camphor, fenchone, cedranone, and isolongifolanone;

aromatic and other ketones such as acetophenone, propiophenone, p-methylacetophenone, p-methoxyacetonphenone, raspberry ketone, methyl benzyl acetone, anisylacetone, anisketone, zingerone, heliotropylacetone, 4-methyl-4-phenyl-2-pentanone, 5-phenyl-5-methyl-3-hexanone, methyl naphthyl ketone, benzophenone, dibenzyl ketone, methyltetrahydrofuranone, acetylfuran, 2-acetyl-5-methylfuran, furfuralacetaone, acetyldimethylacetone, furanol, sotolon, homofuraneol, 5-ethyl-3-hydroxy-4-methyl-2(5H)-furanone, maltol, ethylmaltol, and acetonylmethyltetrahydropyran;

macrocyclic musks such as 3-methylcyclopentadecanone and cyclopentadecanone;

ketones such as ketoesters, such as methyl acetoacetate, ethyl acetoacetate, ethyl 2-hexylacetoacetate, ethyl benzylacetoacetate, methyl levulinate, ethyl levulinate, butyl levulinate, isoamyl levulinate, methyl pyruvate, ethyl pyruvate, methyl dihydrojasmonate and the like may be exemplified.

The dialkoxy compound represented by the following general formula (3) which is a raw material for producing the ether compound in the present invention will be explained below.

[Chem. 6]

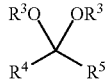

(3)

In the formula, $R^3$ is an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent (provided that a group which is eliminated by hydrogenation is excluded).

$R^4$ is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent.

$R^5$ is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, an aralkyl group which may have a substituent, or —$OR^3$; provided that a case where both of $R^4$ and $R^5$ is a hydrogen atoms is excluded. Further, $R^4$ and $R^5$ may be combined to form a ring.

As the alkyl group having 1 to 20 carbon atoms represented by $R^3$ in the general formula (3), an alkyl group having 1 to 10 carbon atoms is preferred. Specific examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and the like.

As the 3- to 8-membered alicyclic group represented by $R^3$ in the general formula (3), a 5- to 7-membered alicyclic group is preferred. Specific examples thereof include a cyclopropyl group, a cyclobutyl group, a cyclopentyl group, a cyclohexyl group, a cycloheptyl group, a cyclooctyl group, and the like.

As the aryl group represented by $R^3$ in the general formula (3), an aromatic monocyclic group, an aromatic polycyclic group, or an aromatic condensed cyclic group, each having 6 to 20 carbon atoms, is preferred. Specific examples thereof include an aromatic monocyclic or polycyclic group, such as a phenyl group, a naphthyl group, an anthryl group, a phenanthryl group, an indenyl group, and the like. Furthermore, a metallocenyl group such as ferrocenyl group may be exemplified.

As the heterocyclic group represented by $R^3$ in the general formula (3), an aliphatic heterocyclic group and an aromatic heterocyclic group may be mentioned.

As the aliphatic heterocyclic group, examples thereof include 3- to 8-membered, preferably 5- or 6-membered monocyclic, polycyclic, or condensed cyclic ones having 2 to 14 carbon atoms and containing at least one heteroatom, preferably 1 to 3 heteroatoms. As the heteroatom, heteroatoms such as a nitrogen atom, an oxygen atom, and a sulfur atom may be mentioned.

Specific examples of the aliphatic heterocyclic group include an oxiranyl group, an aziridinyl group, a 2-oxopyrrolidyl group, a piperidyl group, a piperadinyl group, a morpholino group, a tetrahydrofuryl group, a tetrahydropyranyl group, a tetrahydrothienyl group, and the like.

On the other hand, as the aromatic heterocyclic group, examples thereof include 5- to 8-membered, preferably 5- or 6-membered monocyclic, polycyclic, or condensed cyclic aromatic heterocyclic (heteroaryl) groups having 2 to 15 carbon atoms and containing at least one heteroatom, preferably 1 to 3 heteroatoms. As the heteroatom, a nitrogen atom, an oxygen atom, a sulfur atom and the like may be mentioned.

Specific examples of the aromatic heterocyclic group include a tetrazinyl group, a furyl group, a thienyl group, a pyridyl group, a pyrinidyl group, a pyrazinyl group, a pyradazinyl group, an imidazoyl group, an oxazoyl group, a thiazoyl group, a benzofuryl group, a benzothienyl group, a quinolyl group, an isoquinolyl group, a quinoxalinyl group, a phthalazinyl group, a quinazolinyl group, a naphthylidinyl group, a cinnolinyl group, a benzimidazoline group, a benzoxazolyl group, a benzothiazolyl group, and the like.

As the aralkyl group (provided that a group which is eliminated by hydrogenation is excluded) represented by $R^3$ in the general formula (3), an aralkyl group having 8 to 20 carbon atoms is preferred. Specific examples thereof include a 2-phenylethyl group, a 2-phenylpropyl group, a 3-phenylpropyl group, and the like.

As the alkyl group having 1 to 20 carbon atoms represented by $R^4$ in the general formula (3), an alkyl group having 1 to 10 carbon atoms is preferred. Specific examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and the like.

As the 3- to 8-membered alicyclic group represented by $R^4$ in the general formula (3), a 5- to 7-membered alicyclic group is preferred. Specific examples thereof include a cyclopropyl group, a cyclobutyl group, a cyclopentyl group, a cyclohexyl group, a cycloheptyl group, a cyclooctyl group, and the like.

As the aryl group represented by $R^4$ in the general formula (3), an aromatic monocyclic group, an aromatic polycyclic group, or an aromatic condensed cyclic group, each having 6 to 20 carbon atoms, is preferred. Specific examples thereof include an aromatic monocyclic or polycyclic group, such as a phenyl group, a naphthyl group, an anthryl group, a phenanthryl group, an indenyl group, and the like. Furthermore, a metallocenyl group such as ferrocenyl group may be exemplified.

As the heterocyclic group represented by $R^4$ in the general formula (3), an aliphatic heterocyclic group and an aromatic heterocyclic group may be mentioned.

As the aliphatic heterocyclic group, examples thereof include 3- to 8-membered, preferably 5- or 6-membered monocyclic, polycyclic, or condensed cyclic ones having 2 to 14 carbon atoms and containing at least one heteroatom, preferably 1 to 3 heteroatoms. As the heteroatom, heteroatoms such as a nitrogen atom, an oxygen atom, and a sulfur atom may be mentioned.

Specific examples of the aliphatic heterocyclic group include an oxiranyl group, an aziridinyl group, a 2-oxopyrrolidyl group, a piperidyl group, a piperadinyl group, a morpholino group, a tetrahydrofuryl group, a tetrahydropyranyl group, a tetrahydrothienyl group, and the like.

On the other hand, as the aromatic heterocyclic group, examples thereof include 5- to 8-membered, preferably 5- or 6-membered monocyclic, polycyclic, or condensed cyclic aromatic heterocyclic (heteroaryl) groups having 2 to 15 carbon atoms and containing at least one heteroatom, preferably 1 to 3 heteroatoms. As the heteroatom, a nitrogen atom, an oxygen atom, a sulfur atom and the like may be mentioned.

Specific examples of the aromatic heterocyclic group include a tetrazinyl group, a furyl group, a thienyl group, a pyridyl group, a pyrinidyl group, a pyrazinyl group, a pyradazinyl group, an imidazoyl group, an oxazoyl group, a thiazoyl group, a benzofuryl group, a benzothienyl group, a quinolyl group, an isoquinolyl group, a quinoxalinyl group, a phthalazinyl group, a quinazolinyl group, a naphthylidinyl group, a cinnolinyl group, a benzimidazoline group, a benzoxazolyl group, a benzothiazolyl group, and the like.

As the aralkyl group represented by $R^4$ in the general formula (3), an aralkyl group having 7 to 20 carbon atoms is preferred. Specific examples thereof include a benzyl group, a 1-phenylethyl group, a 2-phenylethyl group, and the like.

As the alkyl group having 1 to 20 carbon atoms represented by $R^5$ in the general formula (3), an alkyl group having 1 to 10 carbon atoms is preferred. Specific examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and the like.

As the 3- to 8-membered alicyclic group represented by $R^5$ in the general formula (3), a 5- to 7-membered alicyclic group is preferred. Specific examples thereof include a cyclopropyl group, a cyclobutyl group, a cyclopentyl group, a cyclohexyl group, a cycloheptyl group, a cyclooctyl group, and the like.

As the aryl group represented by $R^5$ in the general formula (3), an aromatic monocyclic group, an aromatic polycyclic group, or an aromatic condensed cyclic group, each having 6 to 20 carbon atoms, is preferred. Specific examples thereof include an aromatic monocyclic or polycyclic group, such as a phenyl group, a naphthyl group, an anthryl group, a phenanthryl group, an indenyl group, and the like. Furthermore, a metallocenyl group such as ferrocenyl group may be exemplified.

As the heterocyclic group represented by $R^5$ in the general formula (3), an aliphatic heterocyclic group and an aromatic heterocyclic group may be mentioned.

As the aliphatic heterocyclic group, examples thereof include 3- to 8-membered, preferably 5- or 6-membered monocyclic, polycyclic, or condensed cyclic ones having 2 to 14 carbon atoms and containing at least one heteroatom, preferably 1 to 3 heteroatoms. As the heteroatom, heteroatoms such as a nitrogen atom, an oxygen atom, and a sulfur atom may be mentioned.

Specific examples of the aliphatic heterocyclic group include an oxiranyl group, an aziridinyl group, a 2-oxopyrrolidyl group, a piperidyl group, a piperadinyl group, a morpholino group, a tetrahydrofuryl group, a tetrahydropyranyl group, a tetrahydrothienyl group, and the like.

On the other hand, as the aromatic heterocyclic group, examples thereof include 5- to 8-membered, preferably 5- or 6-membered monocyclic, polycyclic, or condensed cyclic aromatic heterocyclic (heteroaryl) groups having 2 to 15 carbon atoms and containing at least one heteroatom, preferably 1 to 3 heteroatoms. As the heteroatom, a nitrogen atom, an oxygen atom, a sulfur atom and the like may be mentioned.

Specific examples of the aromatic heterocyclic group include a tetrazinyl group, a furyl group, a thienyl group, a pyridyl group, a pyrinidyl group, a pyrazinyl group, a pyradazinyl group, an imidazoyl group, an oxazoyl group, a thiazoyl group, a benzofuryl group, a benzothienyl group, a quinolyl group, an isoquinolyl group, a quinoxalinyl group, a phthalazinyl group, a quinazolinyl group, a naphthylidinyl group, a cinnolinyl group, a benzimidazoline group, a benzoxazolyl group, a benzothiazolyl group, and the like.

As the aralkyl group represented by R⁵ in the general formula (3), an aralkyl group having 7 to 20 carbon atoms is preferred. Specific examples thereof include a benzyl group, a 1-phenylethyl group, a 2-phenylethyl group, and the like.

The case where both of R⁴ and R⁵ is a hydrogen atom is excluded.

In the case where R⁴ and R⁵ are combined to form a ring, the number of ring-member carbon atoms is preferably from 3 to 16. Specific examples thereof include cyclic hydrocarbons such as cyclopropane, cyclobutane, cyclopentane, cyclohexane, cycloheptane, cyclooctane, cyclononane, cyclodecane, cycloundecane, cyclododecane, cyclotridecane, cyclopentadecane, and cyclohexadecane.

Here, the alkyl group, the alicyclic group, the aryl group, the heterocyclic group, and the aralkyl group, which are represented by R³ to R⁵ in the above general formula (3), may have a substituent, and examples of the substituent include an alkyl group, an aryl group, an aralkyl group, an alicyclic group, a halogen atom, a hydroxyl group, an alkoxy group, a trisubstituted organosiylyl group, a carboxyl group, an acyl group, an acyloxy group, a substituted amino group, a heterocyclic group, a nitro group, and the like. Specific examples of individual substituents are the same as in the cases of the substituents in the aforementioned R¹ and R².

Specific examples of the dialkoxy compound represented by the general formula (3) (hereinafter sometimes referred to as "dialkoxy compound (3)") of the present invention include:

orthoesters such as methyl orthoformate, ethyl orthoformate, n-propyl orthoformate, isopropyl orthoformate, n-butyl orthoformate, methyl orthoacetate, ethyl orthoacetate, n-propyl orthoacetate, isopropyl orthoacetate, n-butyl orthoacetate, methyl orthopropionate, ethyl orthopropionate, n-propyl orthopropionate, isopropyl orthopropionate, n-butyl orthopropionate, methyl ortho-n-butyrate, ethyl ortho-n-butyrate, n-propyl ortho-n-butyrate, isopropyl ortho-n-butyrate, n-butyl ortho-n-butyrate, methyl orthoisobutyrate, ethyl orthoisobutyrate, n-propyl orthoisobutyrate, isopropyl orthoisobutyrate, and n-butyl orthoisobutyrate;

acetals such as acetaldehyde dimethyl acetal, acetaldehyde diethyl acetal, acetaldehyde di-n-propyl acetal, acetaldehyde diisopropyl acetal, acetaldehyde di-n-butyl acetal, propylaldehyde dimethyl acetal, propylenaldehyde diethyl acetal, propylenaldehyde di-n-propyl acetal, propylenaldehyde diisopropyl acetal, propylenaldehyde di-n-butyl acetal, butyraldehyde dimethyl acetal, butyraldehyde diethyl acetal, butyraldehyde di-n-propyl acetal, butyraldehyde diisopropyl acetal, butyraldehyde di-n-butyl acetal, cyclopentanecarbaldehyde dimethyl acetal, cyclopentanecarbaldehyde diethyl acetal, cyclopentanecarbaldehyde di-n-propyl acetal, cyclopentanecarbaldehyde diisopropyl acetal, cyclopentanecarbaldehyde di-n-butyl acetal, cyclohexanecarbaldehyde dimethyl acetal, cyclohexanecarbaldehyde diethyl acetal, cyclohexanecarbaldehyde di-n-propyl acetal, cyclohexanecarbaldehyde diisopropyl acetal, cyclohexanecarbaldehyde di-n-butyl acetal, cycloheptanecarbaldehyde dimethyl acetal, cycloheptanecarbaldehyde diethyl acetal, cycloheptanecarbaldehyde di-n-propyl acetal, cycloheptanecarbaldehyde diisopropyl acetal, cycloheptanecarbaldehyde di-n-butyl acetal, benzaldehyde dimethyl acetal, benzaldehyde diethyl acetal, benzaldehyde di-n-propyl acetal, benzaldehyde diisopropyl acetal, benzaldehyde di-n-butyl acetal, phenylacetaldehyde dimethyl acetal, phenylacetaldehyde diethyl acetal, phenylacetaldehyde di-n-propyl acetal, phenylacetaldehyde diisopropyl acetal, and phenylacetaldehyde di-n-butyl acetal;

ketals such as 2,2-dimethoxypropane, 2,2-diethoxypropane, 2,2-di-n-propylpropane, 2,2-diisopropylpropane, 2,2-di-n-butylpropane, 2,2-dimethoxybutane, 2,2-diethoxybutane, 2,2-di-n-propylbutane, 2,2-diisopropylbutane, 2,2-di-n-butylbutane, 2,2-dimethoxypentane, 2,2-diethoxypentane, 2,2-di-n-propylpentane, 2,2-diisopropylpentane, 2,2-di-n-butylpentane, 3,3-dimethoxypentane, 3,3-diethoxypentane, 3,3-di-n-propylpentane, 3,3-diisopropylpentane, 3,3-di-n-butylpentane, cyclopentanone dimethyl ketal, cyclopentanone diethyl ketal, cyclopentanone di-n-propyl ketal, cyclopentanone diisopropyl ketal, cyclopentanone di-n-butyl ketal, cyclohexanone dimethyl ketal, cyclohexanone diethyl ketal, cyclohexanone di-n-propyl ketal, cyclohexanone diisopropyl ketal, cyclohexanone di-n-butyl ketal, cycloheptanone dimethyl ketal, cycloheptanone diethyl ketal, cycloheptanone di-n-propyl ketal, cycloheptanone diisopropyl ketal, and cycloheptanone di-n-butyl ketal; and the like.

The ether compound represented by the following general formula (1) (hereinafter sometimes referred to as "ether compound (1)") which is formed by reacting the compounds represented by the general formulae (2) and (3), will be explained.

[Chem. 7]

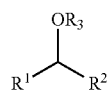

(1)

In the formula, R¹ is an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent.

R² is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent. Further, R¹ and R² may be combined to form a ring.

R³ is an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent (provided that a group which is eliminated by hydrogenation is excluded).

Specific embodiments of R¹ to R³ are the same as in R¹ to R³ explained in the general formula (2) and the general formula (3).

As the ether compound (1) in the present invention, specifically, the following compounds may be exemplified.

Examples thereof include methyl hexyl ether, ethyl hexyl ether, decyl methyl ether, decyl ethyl ether, 3-methoxy-1,1,5-trimethylcyclohexane, 3-ethoxy-1,1,5-trimethylcyclohexane, bornyl methyl ether, bornyl ethyl ether, cyclododecyl methyl ether, cyclododecyl ethyl ether, 1-methylcyclododecyl methyl ether, cedrol methyl ether, methyl benzyl ether, ethyl benzyl ether, methyl phenylethyl ether, ethyl 2-methoxybenzyl ether, isoamyl benzyl ether, isoamyl phenylethyl ether, dibenzyl ether, cyclohexyl phenylethyl ether, 4-(3-ethoxybutyl)phenol, vanillyl ethyl ether, vanillyl butyl ether, and the like.

In the production method of the present invention, it is preferred to conduct the hydrogenation reaction by further adding an alcohol represented by the following general formula (4) as an additional component. Thereby, it becomes possible to freely adjust substrate concentration or acid catalyst concentration, resulting in preferable results such as suppression of by-products and improvement in selectivity.

$$R^3OH \qquad (4)$$

In the formula (4), $R^3$ has the same meaning as the definition of $R^3$ in the general formula (3). Namely, $R^3$ is an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent (provided that a group which is eliminated by hydrogenation is excluded).

As the alkyl group having 1 to 20 carbon atoms represented by $R^3$ in the general formula (4), an alkyl group having 1 to 10 carbon atoms is preferred. Specific examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and the like.

As the 3- to 8-membered alicyclic group represented by $R^3$ in the general formula (4), a 5- to 7-membered alicyclic group is preferred. Specific examples thereof include a cyclopentyl group, a cyclohexyl group, a cycloheptyl group, a cyclooctyl group, and the like.

As the aryl group represented by $R^3$ in the general formula (4), an aromatic monocyclic group, an aromatic polycyclic group, or an aromatic condensed cyclic group, each having 6 to 20 carbon atoms, is preferred. Specific examples thereof include an aromatic monocyclic or polycyclic group, such as a phenyl group, a naphthyl group, an anthryl group, a phenanthryl group, an indenyl group, and the like. Furthermore, a metallocenyl group such as ferrocenyl group may be exemplified.

As the heterocyclic group represented by $R^3$ in the general formula (4), an aliphatic heterocyclic group and an aromatic heterocyclic group may be mentioned.

As the aliphatic heterocyclic group, examples thereof include 3- to 8-membered, preferably 5- or 6-membered monocyclic, polycyclic, or condensed cyclic ones having 2 to 14 carbon atoms and containing at least one heteroatom, preferably 1 to 3 heteroatoms. As the heteroatom, heteroatoms such as a nitrogen atom, an oxygen atom, and a sulfur atom may be mentioned.

Specific examples of the aliphatic heterocyclic group include an oxiranyl group, an aziridinyl group, a 2-oxopyrrolidyl group, a piperidyl group, a piperadinyl group, a morpholino group, a tetrahydrofuryl group, a tetrahydropyranyl group, a tetrahydrothienyl group, and the like.

On the other hand, as the aromatic heterocyclic group, examples thereof include 5- to 8-membered, preferably 5- or 6-membered monocyclic, polycyclic, or condensed cyclic aromatic heterocyclic (heteroaryl) groups having 2 to 15 carbon atoms and containing at least one heteroatom, preferably 1 to 3 heteroatoms. As the heteroatom, a nitrogen atom, an oxygen atom, a sulfur atom and the like may be mentioned.

Specific examples of the aromatic heterocyclic group include a tetrazinyl group, a furyl group, a thienyl group, a pyridyl group, a pyrinidyl group, a pyrazinyl group, a pyradazinyl group, an imidazoyl group, an oxazoyl group, a thiazoyl group, a benzofuryl group, a benzothienyl group, a quinolyl group, an isoquinolyl group, a quinoxalinyl group, a phthalazinyl group, a quinazolinyl group, a naphthylidinyl group, a cinnolinyl group, a benzimidazoline group, a benzoxazolyl group, a benzothiazolyl group, and the like.

As the aralkyl group (provided that a group which is eliminated by hydrogenation is excluded) represented by $R^3$ in the general formula (4), an aralkyl group having 8 to 20 carbon atoms is preferred. Specific examples thereof include a 2-phenylethyl group, a 2-phenylpropyl group, a 3-phenylpropyl group, and the like.

Here, the alkyl group, the alicyclic group, the aryl group, the heterocyclic group, and the aralkyl group, represented by $R^3$ in the above general formula (4), may have a substituent, and examples of the substituent include an alkyl group, an aryl group, an aralkyl group, an alicyclic group, a halogen atom, a hydroxyl group, an alkoxy group, a trisubstituted organosiylyl group, a carboxyl group, an acyl group, an acyloxy group, a substituted amino group, a heterocyclic group, a nitro group, and the like. Specific examples of individual substituents are the same as in the cases of the substituents in the aforementioned $R^1$ and $R^2$.

Specific examples of the alcohol represented by the general formula (4) in the present invention include:
saturated aliphatic alcohols having 1 to 20 carbon atoms, such as methanol, ethanol, n-propanol, isopropanol, n-butanol, isobutanol, sec-butanol, tert-butanol, pentanol, hexanol, heptanol, octanol, nonanol, decanol, dodecanol, undecanol, tridecanol, tetradecanol, pentadecanol, hexadecanol, heptadecanol, octadecanol, nonadecanol, and eicosanol;
3- to 8-membered cycloalkyl alcohols such as cyclopropyl alcohol, cyclobutyl alcohol, cyclopentyl alcohol, cyclohexyl alcohol, cycloheptyl alcohol, and cyclooctyl alcohol;
phenols such as phenol, cresol, xylenol, α-naphthol, β-naphthol, anthrol, and phenanthrol.

In the method of the present invention, the ether compound represented by the general formula (1) can be produced by a hydrogenation reaction of the carbonyl compound represented by the general formula (2) and the dialkoxy represented by the general formula (3) in the presence of a hydrogenation catalyst and an acidic substance.

As the hydrogenation catalyst for use in the hydrogenation reaction to be used in the present invention, heterogeneous hydrogenation catalysts commonly frequently used are preferably used. As the heterogeneous hydrogenation catalysts, examples thereof include Raney nickel, platinum oxide, platinum black, palladium black, rhodium black, palladium carbon, iridium carbon, rhodium carbon, ruthenium carbon, osmium carbon, palladium alumina, palladium silica, palladium silica alumina, and the like.

Preferable examples thereof include Raney nickel, platinum black, palladium black, palladium carbon, palladium alumina, palladium silica, palladium silica alumina, and the like. Of these, Raney nickel, palladium black, palladium carbon, and the like are more preferred because of high reaction selectivity and yields and high versatility.

As the acidic substance to be used in the method of the present invention, various acidic substances such as Brønsted acids and Lewis acids can be used.

Examples of the acidic substance include: sulfonic acids such as benzenesulfonic acid, p-toluenesulfonic acid, methanesulfonic acid, camphorsulfonic acid, and sulfuric acid;

Brensted acids such as perhalogenoacetic acids, such as trifluoroacetic acid, trichloroacetic acid, and the like; and Lewis acids such as ferric chloride (iron(III) chloride), zinc chloride, and stannic chloride (tin(IV) chloride); and the like.

As preferred acidic substances, examples thereof include p-toluenesulfonic acid, methanesulfonic acid, camphorsulfonic acid, and the like. Of these, p-toluenesulfonic acid, sulfuric acid, and the like are more preferred because of their versatility and high reaction selectivity and yields. These acidic substances may be used singly or two or more thereof may be used but a method using one kind thereof is preferred.

The reaction may be carried out in an organic solvent. As the organic solvent, an organic solvent which does not exert an adverse effect on the production method of the present invention may be used, or the alcohol represented by the general formula (4) to be added as an additional component may be used as the solvent.

Also, as other organic solvents, examples thereof include aromatic hydrocarbons such as toluene, benzene, and chlorobenzene; aliphatic esters such as ethyl acetate, propyl acetate, and butyl acetate; ether compounds such as diethyl ether, diisopropyl ether, and tetrahydrofuran; halogenated hydrocarbons such as dichloromethane and dichloroethane; and the like.

They may be used singly or may be used as a mixed solution of two or more thereof. Preferable examples of the solvent include the alcohol represented by the general formula (4), an aromatic hydrocarbon, and the like. Of these, the alcohol represented by the general formula (4), toluene, and the like may be mentioned. Furthermore, of these, the alcohol represented by the general formula (4) is more preferred because of high reaction selectivity and yields.

Moreover, the amount of the solvent to be used is not particularly limited but is in the range of about 0.1 to 10 equivalents in volume, preferably about 0.5 to 3 equivalents in volume relative to the carbonyl compound (2).

In the present invention, with regard to the mixing ratio of the carbonyl compound (2) to the dialkoxy compound (3), the dialkoxy compound (3) is preferably about from 1.0 to 20.0 moles and is preferably about from 1.1 to 5.0 moles, relative to 1 mole of the carbonyl compound (2).

In the present invention, in the case where the alcohol (4) is not used as a solvent and is added as an additional component, with regard to the mixing ratio of the carbonyl compound (2) to the alcohol (4), the alcohol (4) is preferably about from 0.1 to 20.0 moles and is preferably about from 1.0 to 5.0 moles, relative to 1 mole of the carbonyl compound (2).

The amount of the heterogeneous hydrogenation catalyst to be used in the present invention is preferably in the range of about 0.02 to 20% by weight, more preferably 0.1 to about 5% by weight, relative to 1% by weight of the carbonyl compound (2), but the amount is not limited to the range.

Moreover, the amount of the acidic substance to be used in the reaction is in the range of about 0.1 to 10% by weight, more preferably about 0.5 to 5% by weight, relative to 1% by weight of the carbonyl compound (2), but the amount is not limited to the range.

Hydrogen pressure is preferably in the range of about 0.05 to 10 MPa, more preferably about 0.1 to 3 MPa, but is not limited thereto.

As reaction temperature, a range of about 20 to 100° C., preferably about 30 to 60° C. is adopted. The hydrogenation reaction can be smoothly carried out by the reaction for about 1 to 50 hours, preferably 1 to 10 hours while maintaining the above-described temperature.

After the reaction is completed, the heterogeneous hydrogenation catalyst is removed by filtration from the reaction solution obtained by the above reaction, and then, the solvent is removed under reduced pressure. There may be adopted a method of purifying the resulting residue by distillation under reduced pressure, a method of purifying it by silica gel column chromatography, a method of purifying it by recrystallization method, and the like.

EXAMPLES

The following will describe the present invention in detail with reference to Examples, but the present invention should not be construed as being limited to these Examples.

Analyses in the present Examples were conducted using the following analytical instruments.

Gas Chromatographic (GC) Quantitative Determination [internal standard quantitative determination]

Instrument: GC-4000 (manufactured by G L Sciences Inc.)

Column: RTX-1 (30 cm in length×0.25 mm in inner diameter, Liquid phase film thickness: 0.25 μm)

Proton Nuclear Magnetic Resonance ($^1$H-NMR)

Instrument: AVANCEIII500 Model (500 MHz) (manufactured by Bruker BioSpin K.K.)

Example 1: Synthesis (a) of Vanillyl Ethyl Ether 3.04 g (20.0 mmol) of vanillin, 5.93 g (40.0 mmol) of ethyl orthoformate, 15.0 mg of p-toluenesulfonic acid monohydrate, and 15.0 mg of 5% palladium carbon were added into a 100 ml autoclave (using an inner tube). After the inside of the system was substituted with nitrogen, substitution with hydrogen was performed and 3.0 MPa of a hydrogen gas was enclosed. The temperature in the autoclave was controlled to 130° C. and stirring was continued for 1 hour. After the stirring, the reaction solution was cooled and then the hydrogen gas was purged. Thereafter, the palladium catalyst was removed by filtration operation and ethyl orthoformate was collected under reduced pressure to thereby obtain 3.60 g (value at internal standard quantitative determination: 97.4 wt %, yield: 96.2%) of vanillyl ethyl ether.

$^1$H-NMR (CDCl$_3$): σ=1.37 (3H, t), 3.42 (1H, q), 3.86 (3H, s), 4.44 (2H, s), 5.92 (1H, s), 6.88 (3H, m)

Example 2: Synthesis (b) of Vanillyl Ethyl Ether 1.52 g (10.0 mmol) of vanillin, 2.96 g (20.0 mmol) of ethyl orthoformate, 4.5 mg of boron trifluoride diethyl ether complex, and 7.5 mg of 5% palladium carbon were added into a 100 ml autoclave (using an inner tube). After the inside of the system was substituted with nitrogen, substitution with hydrogen was performed and 3.0 MPa of a hydrogen gas was enclosed. The temperature in the autoclave was controlled to 80° C. and stirring was continued for 1 hour. After the stirring, the reaction solution was cooled and then the hydrogen gas was purged. Thereafter, the palladium catalyst was removed by filtration operation and ethyl orthoformate was collected under reduced pressure to thereby obtain 1.84 g (value at internal standard quantitative determination: 74.5 wt %, yield: 75.3%) of vanillyl ethyl ether.

$^1$H-NMR (CDC$_3$): σ=1.37 (3H, t), 3.42 (1H, q), 3.86 (3H, s), 4.44 (2H, s), 5.92 (1H, s), 6.88 (3H, m)

Example 3: Synthesis of 2-methoxyethylbenzene 2.40 g (20.0 mmol) of 2-phenylacetaldehyde, 4.25 g (40.0 mmol) of methyl orthoformate, 2.4 ml of methanol, 12.0 mg of p-toluenesulfonic acid monohydrate, and 60.0 mg of 5% palladium carbon were added into a 100 ml autoclave (using an inner tube). After the inside of the system was substituted with nitrogen, substitution with hydrogen was performed and 3.0 MPa of hydrogen gas was enclosed. The temperature in the autoclave was controlled to 130° C. and stirring was continued for 6 hours. After the stirring, the reaction solution was cooled and then the hydrogen gas was purged. Thereafter, the palladium catalyst was removed by filtration operation, and methanol and excess methyl orthoformate were collected under normal pressure to thereby obtain 2.82 g (value at internal standard quantitative determination: 64.2 wt %, yield: 66.5%) of 2-methoxyethylbenzene.

$^1$H-NMR (CDC$_3$): σ=2.89 (2H, t), 3.38 (3H, s), 3.58 (2H, t), 7.19-7.27 (5H, m)

Example 4: Synthesis (a) of 3-ethoxy-1,1,5-trimethylcyclohexane 2.80 g (20.0 mmol) of 3,3,5-trimethylcyclohexanone, 5.93 g (40.0 mmol) of ethyl orthoformate, 2.8 ml of ethanol, 14.0 mg of p-toluenesulfonic acid monohydrate, and 70.0 mg of 5% palladium carbon were added into a 100 ml autoclave (using an inner tube). After the inside of the system was substituted with nitrogen, substitution with hydrogen was performed and 3.0 MPa of hydrogen gas was enclosed. The temperature in the autoclave was controlled to 130° C. and stirring was continued for 7 hours. After the stirring, the reaction solution was cooled and then the hydrogen gas was purged. Thereafter, the palladium catalyst was removed by filtration operation, and ethanol and excess ethyl orthoformate were collected under normal pressure to thereby obtain 3.12 g (value at internal standard quantitative determination: 96.7 wt %, yield: 88.6%) of 3-ethoxy-1,1,5-trimethylcyclohexane.

$^1$H-NMR (CDC$_3$): σ=0.86 (6H, m), 1.07 (3H, d), 1.17 (3H, t), 1.39 (1H, m), 1.69-1.91 (6H, m), 3.37 (1H, m), 3.52 (1H, m), 3.62 (1H, m)

Example 5: Synthesis (b) of 3-ethoxy-1,1,5-trimethylcyclohexane 2.80 g (20.0 mmol) of 3,3,5-trimethylcyclohexanone, 5.93 g (40.0 mmol) of ethyl orthoformate, 14.0 mg of p-toluenesulfonic acid monohydrate, and 70.0 mg of 5% palladium carbon were added into a 100 ml autoclave (using an inner tube). After the inside of the system was substituted with nitrogen, substitution with hydrogen was performed and 3.0 MPa of hydrogen gas was enclosed. The temperature in the autoclave was controlled to 130° C. and stirring was continued for 7 hours. After the stirring, the reaction solution was cooled and then the hydrogen gas was purged. Thereafter, the palladium catalyst was removed by filtration operation and ethanol and excess ethyl orthoformate were collected under normal pressure to thereby obtain 3.03 g (value at internal standard quantitative determination: 90.7 wt %, yield: 80.8%) of 3-ethoxy-1,1,5-trimethylcyclohexane.

$^1$H-NMR (CDC$_3$): σ=0.86 (6H, m), 1.07 (3H, d), 1.17 (3H, t), 1.39 (1H, m), 1.69-1.91 (6H, m), 3.37 (1H, m), 3.52 (1H, m), 3.62 (1H, m)

Example 6: Synthesis (c) of 3-ethoxy-1,1,5-trimethylcyclohexane 1.40 g (10.0 mmol) of 3,3,5-trimethylcyclohexanone, 2.64 g (20.0 mmol) of 2,2-diethoxypropane, 7.0 mg of p-toluenesulfonic acid monohydrate, and 35.0 mg of 5% palladium carbon were added into a 100 ml autoclave (using an inner tube). After the inside of the system was substituted with nitrogen, substitution with hydrogen was performed and 3.0 MPa of hydrogen gas was enclosed. The temperature in the autoclave was controlled to 130° C. and stirring was continued for 7 hours. After the stirring, the reaction solution was cooled and then the hydrogen gas was purged. Thereafter, the palladium catalyst was removed by filtration operation, and ethanol and excess 2,2-diethoxypropane were collected under normal pressure to thereby obtain 1.61 g (value at internal standard quantitative determination: 90.1 wt %, yield: 85.3%) of 3-ethoxy-1,1,5-trimethylcyclohexane.

$^1$H-NMR (CDC$_3$): σ=0.86 (6H, m), 1.07 (3H, d), 1.17 (3H, t), 1.39 (1H, m), 1.69-1.91 (6H, m), 3.37 (1H, m), 3.52 (1H, m), 3.62 (1H, m)

Example 7: Synthesis of 4-(3-ethoxybutyl)phenol 1.00 g (6.09 mmol) of raspberry ketone, 3.61 g (24.36 mmol) of ethyl orthoformate, 5.0 ml of ethanol, and 50.0 mg of p-toluenesulfonic acid monohydrate, and 10.0 mg of 5% palladium carbon were added into a 100 ml autoclave (using an inner tube). After the inside of the system was substituted with nitrogen, substitution with hydrogen was performed and 1.0 MPa of hydrogen gas was enclosed. The temperature in the autoclave was controlled to 130° C. and stirring was continued for 1 hour. After the stirring, the reaction solution was cooled and then the hydrogen gas was purged. Thereafter, the palladium catalyst was removed by filtration operation, and ethanol and excess ethyl orthoformate were collected under reduced pressure to thereby obtain 1.20 g (value at internal standard quantitative determination: 63.7 wt %, yield: 64.8%) of 4-(3-ethoxybutyl)phenol.

$^1$H-NMR (CDC$_3$): σ=1.16 (3H, d), 1.21 (3H, t), 1.66 (1H, m), 1.80 (1H, m), 2.61 (2H, m), 3.40 (2H, m), 3.57 (1H, m), 6.75 (2H, d), 7.05 (2H, d)

Example 8: Synthesis of Bornyl Methyl Ether 1.52 g (10.0 mmol) of camphor, 5.31 g (50.0 mmol) of methyl orthoformate, 1.5 ml of methanol, 15.0 mg of concentrated sulfuric acid, and 38.0 mg of 5% palladium carbon were added into a 100 ml autoclave (using an inner tube). After the inside of the system was substituted with nitrogen, substitution with hydrogen was performed and 3.0 MPa of hydrogen gas was enclosed. The temperature in the autoclave was controlled to 40° C. and stirring was continued for 24 hours. After the stirring, the reaction solution was cooled and then the hydrogen gas was purged. Thereafter, the palladium catalyst was removed by filtration operation and, after the solution was neutralized with an aqueous sodium hydroxide solution, methanol and excess methyl orthoformate were collected under normal pressure to thereby obtain 1.52 g (value at internal standard quantitative determination: 89.1 wt %, yield: 80.5%) of bornyl methyl ether.

$^1$H-NMR (CDC$_3$): σ=0.80 (3H, s), 0.88 (3H, s), 0.98 (3H, s), 1.44-1.76 (5H, m), 3.18 (1H, m), 3.30 (3H, s), 3.32 (1H, m), 3.47 (1H, m)

While the present invention has been described in detail and with reference to specific embodiments thereof, it will be apparent to one skilled in the art that various changes and modifications can be made therein without departing from the spirit and scope thereof.

The present application is based on Japanese Patent Application No. 2012-026444 filed on Feb. 9, 2012, the contents of which are incorporated herein by reference.

INDUSTRIAL APPLICABILITY

According to the present invention, ether compounds useful as pharmaceuticals, agricultural chemicals, functional materials, fragrances and cosmetics, components of various chemicals, or their raw materials, their synthetic intermediates, and the like can be produced in high yields with high efficiency.

The invention claimed is:

1. A method for producing an ether compound represented by the following general formula (1) through one step, which is a step of reacting a carbonyl compound represented by the following general formula (2) and a dialkoxy compound represented by the following general formula (3) with hydrogen in the presence of a hydrogenation catalyst and an acidic substance to perform hydrogenation:

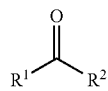

(2)

wherein R$^1$ is an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent;

R$^2$ is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent; and R$^1$ and R$^2$ may be combined to form a ring,

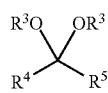

(3)

wherein R$^3$ is an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent provided that a group which is eliminated by hydrogenation is excluded;

R$^4$ is a hydrogen atom, an alkyl group having 1 to 20 carbon atoms which may have a substituent, a 3- to 8-membered alicyclic group which may have a substituent, an aryl group which may have a substituent, a heterocyclic group which may have a substituent, or an aralkyl group which may have a substituent;

R$^5$ is a group represented by —OR$^3$;

and further R$^4$ and R$^5$ may be combined to form a ring,

(1)

wherein definitions of R$^1$ to R$^3$ have the same meanings as described above, and wherein an alcohol represented by the following general formula (4) is used in combination as an additional component:

R$^3$OH (4)

wherein a definition of R$^3$ has the same meaning as described above; and wherein:

the mixing ratio of the carbonyl compound to the dialkoxy compound is 1 mole: 1.1-5.0 moles;

the acidic substance is at least one selected from the group consisting of benzenesulfonic acid, p-toluenesulfonic acid, methanesulfonicacid, camphorsulfonic acid, sulfuric acid, trifluoroacetic acid, ferric chloride, zinc chloride, stannic chloride, and zinc bromide;

the hydrogenation catalyst is a heterogeneous hydrogenation catalyst containing at least one metal selected from the group consisting of palladium, iridium, rhodium, ruthenium, nickel and osmium;

a ratio of the acidic substance to the carbonyl compound (acidic substance/carbonyl compound) is in a range of 0.0030 to 0.05 in terms of weight; and a ratio of the heterogeneous hydrogenation catalyst to the carbonyl compound (heterogeneous hydrogenation catalyst/carbonyl compound) is in a range of 0.1 to 5% by weight.

2. The production method according to claim 1, wherein the carbonyl compound is selected from the group consisting of vanillin, 2-phenylacetaldehyde, 3,3,5-trimethylcyclohexanone, raspberry ketone, and camphor.

3. The production method according to claim 1, wherein the mixing ratio of the carbonyl compound to the dialkoxy compound is 1 mole: 4-5 moles.

* * * * *